(12) United States Patent
Neatrour

(10) Patent No.: US 8,555,727 B2
(45) Date of Patent: Oct. 15, 2013

(54) INTEGRATED VACUUM GAUGE AND REGULATOR

(75) Inventor: Joel David Neatrour, Johnstown, PA (US)

(73) Assignee: DeVilbiss Healthcare, LLC, Somerset, PA (US)

( * ) Notice: Subject to any disclaimer, the term of this patent is extended or adjusted under 35 U.S.C. 154(b) by 345 days.

(21) Appl. No.: 13/158,680

(22) Filed: Jun. 13, 2011

(65) Prior Publication Data

US 2012/0315156 A1    Dec. 13, 2012

(51) Int. Cl.
*G01L 7/00*     (2006.01)

(52) U.S. Cl.
USPC .............................. 73/700; 73/1.02; 73/23.2

(58) Field of Classification Search
None
See application file for complete search history.

(56) References Cited

U.S. PATENT DOCUMENTS

| | | | |
|---|---|---|---|
| 4,558,587 A * | 12/1985 | Fruzzetti | 73/40.7 |
| 5,054,249 A * | 10/1991 | Rankin | 451/99 |
| 5,466,229 A * | 11/1995 | Elson et al. | 604/317 |
| 5,755,224 A | 5/1998 | Good et al. | |
| 6,309,442 B1 * | 10/2001 | Usher | 75/386 |
| 6,318,407 B1 | 11/2001 | Kohn et al. | |
| 7,255,127 B2 | 8/2007 | Davidson et al. | |
| 7,331,250 B2 * | 2/2008 | Hunter | 73/865.9 |
| 7,434,485 B2 * | 10/2008 | Hunter | 73/865.9 |
| 7,441,460 B2 | 10/2008 | Krupa et al. | |
| 7,472,581 B2 * | 1/2009 | Kitazawa et al. | 73/49.2 |
| 8,347,689 B2 * | 1/2013 | Arvaneh | 73/40 |
| 2009/0272444 A1 | 11/2009 | Clementi et al. | |
| 2011/0286859 A1 * | 11/2011 | Ortiz et al. | 417/20 |

* cited by examiner

Primary Examiner — Lisa Caputo
Assistant Examiner — Jermaine Jenkins
(74) Attorney, Agent, or Firm — Fox Rothschild LLP; Dennis M. Carleton

(57) ABSTRACT

An integral regulator and gauge for a vacuum device consists of a circular regulator having the vacuum gauge inside thereof such that the regulator and gauge rotate about a common radial axis. An opening defined in a boss extending from the bottom of the regulator engages a sloped shoulder defined on the inside surface of a circular port in which the regulator is disposed, varying the size of an opening which allows air to bleed into the vacuum chamber to regulate the strength of the vacuum.

20 Claims, 9 Drawing Sheets

_US 8,555,727 B2_

INTEGRATED VACUUM GAUGE AND REGULATOR

FIELD OF THE INVENTION

The present invention is directed to the field of devices providing and regulating vacuum, and, in particular, to such devices for use in medical appellations.

BACKGROUND OF THE INVENTION

Devices generating and utilizing a vacuum are well known in the art. For medical applications, such devices may be used, for example, to provide surgical suction for extracting liquids or semi-liquids from the body during surgery or dentistry, or for aspirators used for clearing the airway, mouth, and nasal passages of persons having chronic airway management issues, or, in the case of emergency, medical aspirators used to clear the airways of traumatized persons Such devices generally consist of a pump for providing negative air pressure connected to a manifold which may also connect a regulator and a vacuum gauge, and a tool for utilizing the vacuum. The regulator allows the regulation and setting of the strength of the vacuum, which, for medical applications may range from around 50 mmHg to over 500 mmHg. The gauge shows the strength of the vacuum, typically expressed in mmHg or inches-Hg.

Regulation of the strength of the vacuum is typically controlled by regulating the amount of air that enters the manifold, and may be limited by the size or strength of the pump used to create the negative air pressure. Allowing air to bleed into the manifold will tend to weaken the vacuum, while sealing the manifold or limiting the amount of air allowed to bleed into the manifold will generally strengthen the vacuum, to the limits of the pump.

The present state of the art is to have a separate regulator and gauge, separately connected to the manifold. This tends to complicate the design of the manifold and the device housing and increase the parts count for the device, thereby also increasing the cost of the device. It would be desirable to provide a combination regulator/gauge able to be connected to the manifold at a single connection point.

SUMMARY OF THE INVENTION

The present invention consists of a unitary, integrated regulator and gauge that provides ease of use for the user of the device, which connects to the device manifold at a single point, which exits the devices housing at a single point and which reduces the parts count, and therefore the cost, of the device.

The device consists of a commercially available, off the shelf vacuum gauge which has been inserted into a funnel-shaped regulator having a cylindrical-shaped boss defined thereon. The regulator may be connected to the manifold via a stationary housing or aperture in which the regulator may be rotated. The regulator defines an opening in the boss portion thereof. The boss contacts a cylindrical surface, preferably an interface to the manifold, having a generally helical-shaped, sloped shoulder defined on the inner surface thereof. As the regulator is turned, the generally helical-shaped shoulder blocks an increasingly-larger portion of the opening defined in the boss, thereby allowing less air to bleed into the manifold. Turning the regulator in the opposite direction allows more of the opening in the boss to be exposed, thereby allowing more air to bleed into the manifold.

The gauge is preferably concentrically aligned with the regulator, such that when the regulator is rotated, the gauge rotates with it. This gives the effect of the needle of the gauge being stationary, as with a magnetic compass, with the markings of the scale of the gauge moving thereunder, as the strength of the vacuum varies due to the rotation of the regulator.

DETAILED DESCRIPTION OF THE INVENTION

Figure 1:
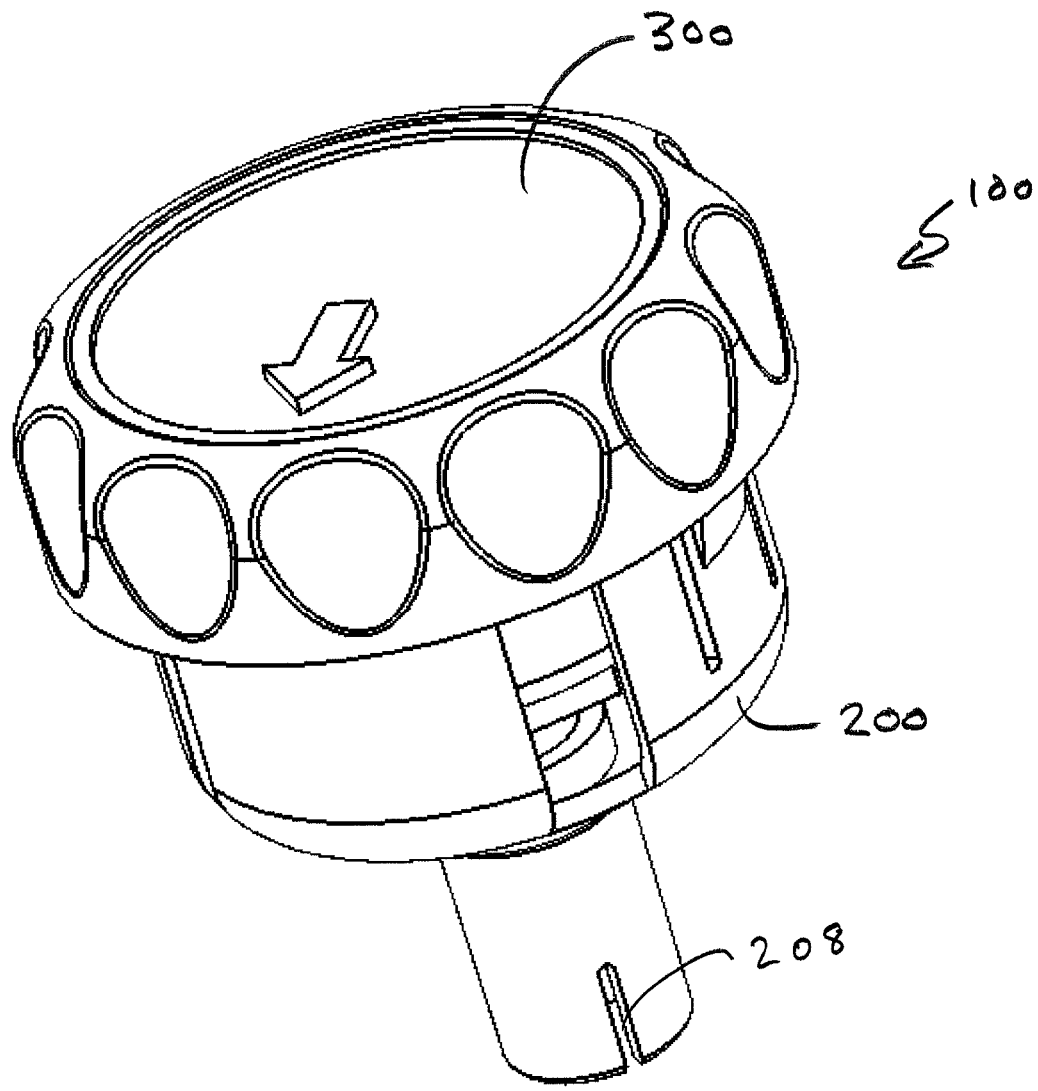
FIG. 1 is a perspective view of the regulator/gauge assembly.

The device of the invention, shown essentially in FIG. 1, is intended to be integrated into the housing of devices requiring control of a vacuum, such as an aspirator or a surgical suction device. The assembly 100 device shown in FIG. 1 consists essentially of regulator 200 and vacuum gauge 300, oriented coaxially and fitted together, preferably with an interference fit, such that rotation of regulator 200 will also cause vacuum gauge 300 to rotate.

Figure 2:
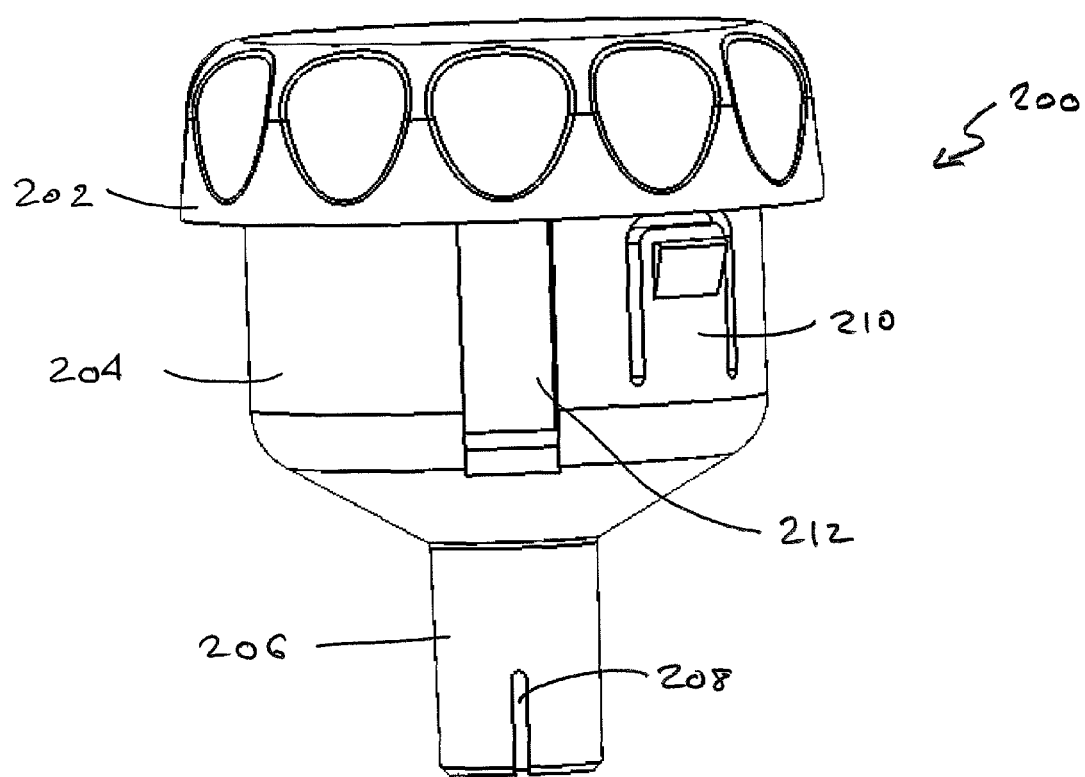
FIG. 2 is a perspective view of the regulator element.
Figure 3:
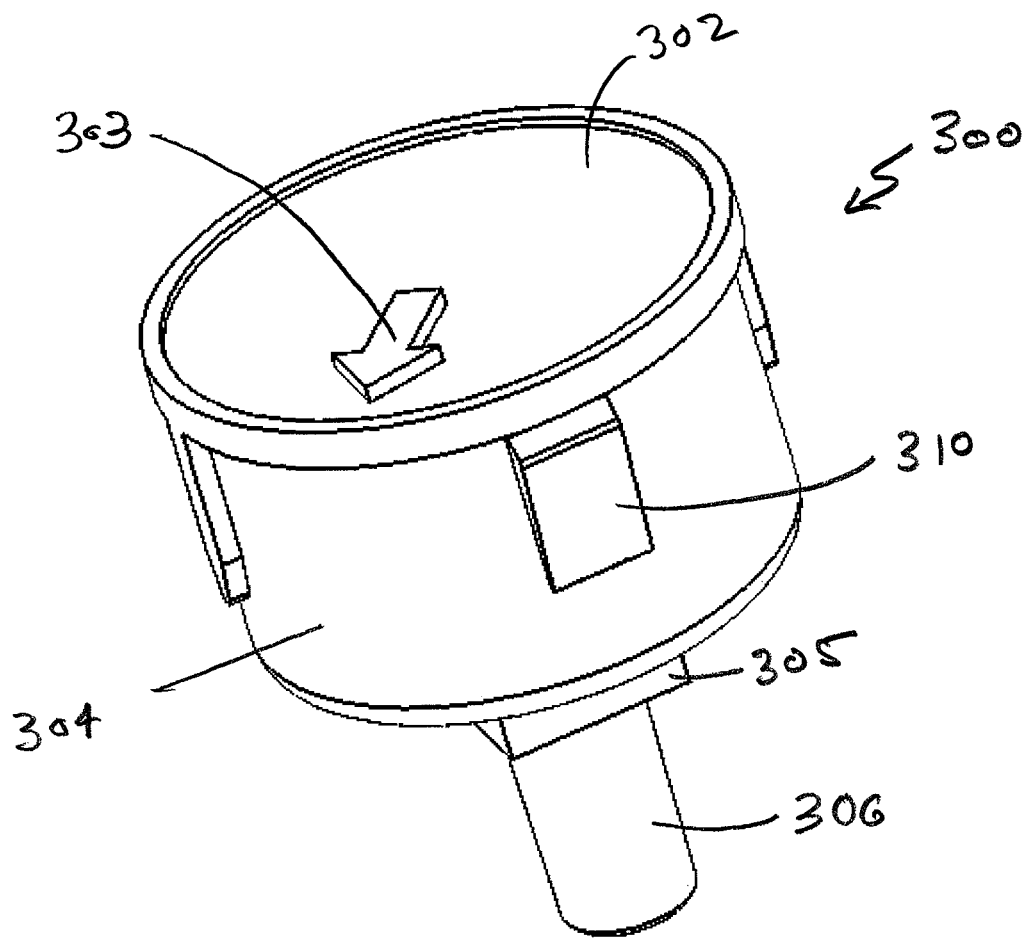
FIG. 3 is a perspective view of the gauge element.

Regulator 200, shown in FIG. 2, consists of cylindrical body portion 204 which tapers to cylindrical boss portion 206. Boss portion 206 defines an opening 208 therein, the purpose of which will be discussed later. A beveled portion 202 is disposed at the top of cylindrical body 204 and may have integrated finger depressions defined thereon to assist a user in rotating regulator/gauge assembly 100.

The vacuum gauge 300 consists essentially of commercially available off the shelf vacuum gauge having the proper scale. The body of the vacuum gauge is inserted into the body of regulator 200 and engages regulator 200 via tabs 310 which engage opening 212 defined in the cylindrical body 204 of regulator 200. The exact configuration of the tabs and indentations defined in cylindrical body 204 of regulator 200 is dependent on the configuration of the vacuum gauge selected and is not part of the invention.

Stem 306 on vacuum gauge 300 is a fitting which typically would be utilized to fit the gauge to a manifold or pipe containing the vacuum therein. However, stem 306 will fit inside boss 206 of regulator 200. Stem 306 of gauge 300 may define threads thereon which may fit on the inside surface of boss 206 via an interference fit or boss 206 may have reciprocal threads defined on the inner surface thereof. Preferably, when gauge 300 is fitted inside regulator 200, stem 306 does not extend past opening 208.

Figure 4A:
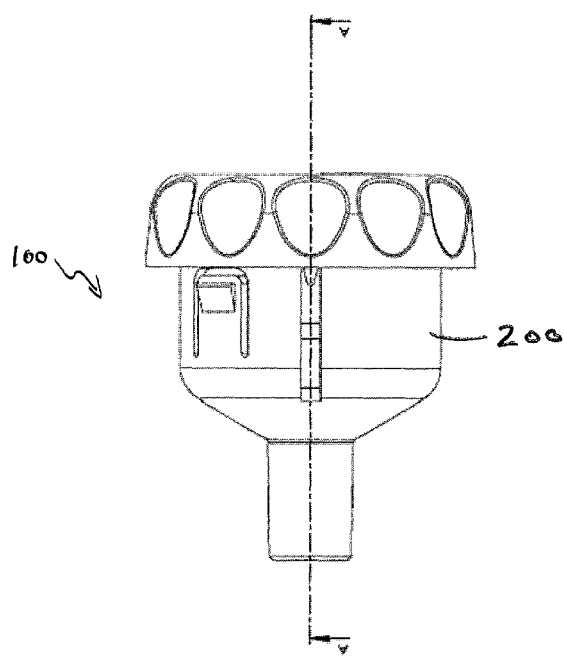
FIG. 4a is a side plan view of the regulator/gauge assembly showing cross section A-A
Figure 4B:
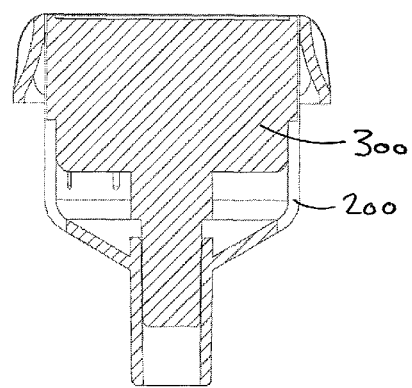
FIG. 4b is a cross section view of the device of FIG. 4a along line A-A.

Regulator 200 and gauge 300 are shown in an assembled version in FIG. 4a and in the cross sectional version in FIG.

4b. Preferably, regulator 200 and gauge 300 will be radially aligned with each other, such that the both rotate around the same axis of rotation.

Figure 5:
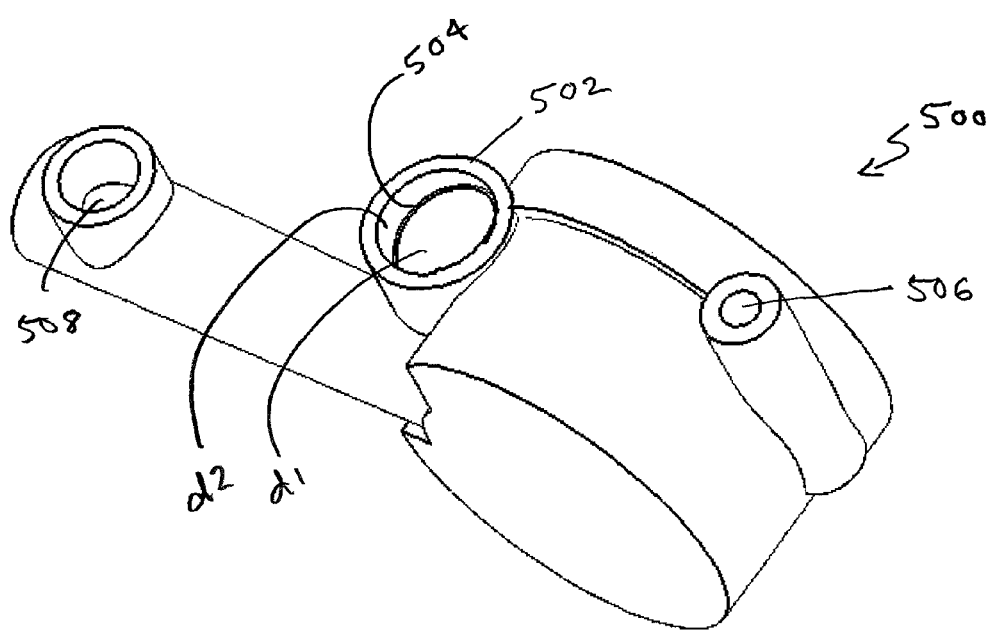
FIG. 5 shows one embodiment of a manifold.

FIG. 5 shows a typical manifold 500 of a suction device. Included in manifold 500 is fitting 502 to which regulator/gauge assembly 100 would be attached. Pump connection 508 and exhaust port 506. Defined within port 502 is sloped shoulder 504, which, in the preferred embodiment, is helical in shape. The inside surface of port 502 has a first cylindrical portion defined below the shoulder, of diameter d1, where d1 is approximately the same diameter as outside diameter of boss portion 206 of regulator 200. Boss portion 206 of regulator 200 is meant to rotate within the portion of port 502 having diameter d1. A second portion of port 502, located above shoulder 504, has a diameter d2 which is larger than diameter d1 by the width of shoulder 504.

Shoulder 504 spirals up the inside surface of port 502 such that when regulator 200 is rotated therein, varying portions of opening 208 are exposed or covered up, depending upon the direction and extent of the rotation. When opening 208 is completely covered, this will represent the maximum vacuum available. As more and more of opening 208 is exposed via rotation of the regulator 200, more air is allowed to bleed into the interior volume of manifold 500 via the space defined between boss 206 and the portion of port 502 having diameter d2 (See reference number 506 in FIG. 6), thereby weakening the vacuum.

Figure 6:
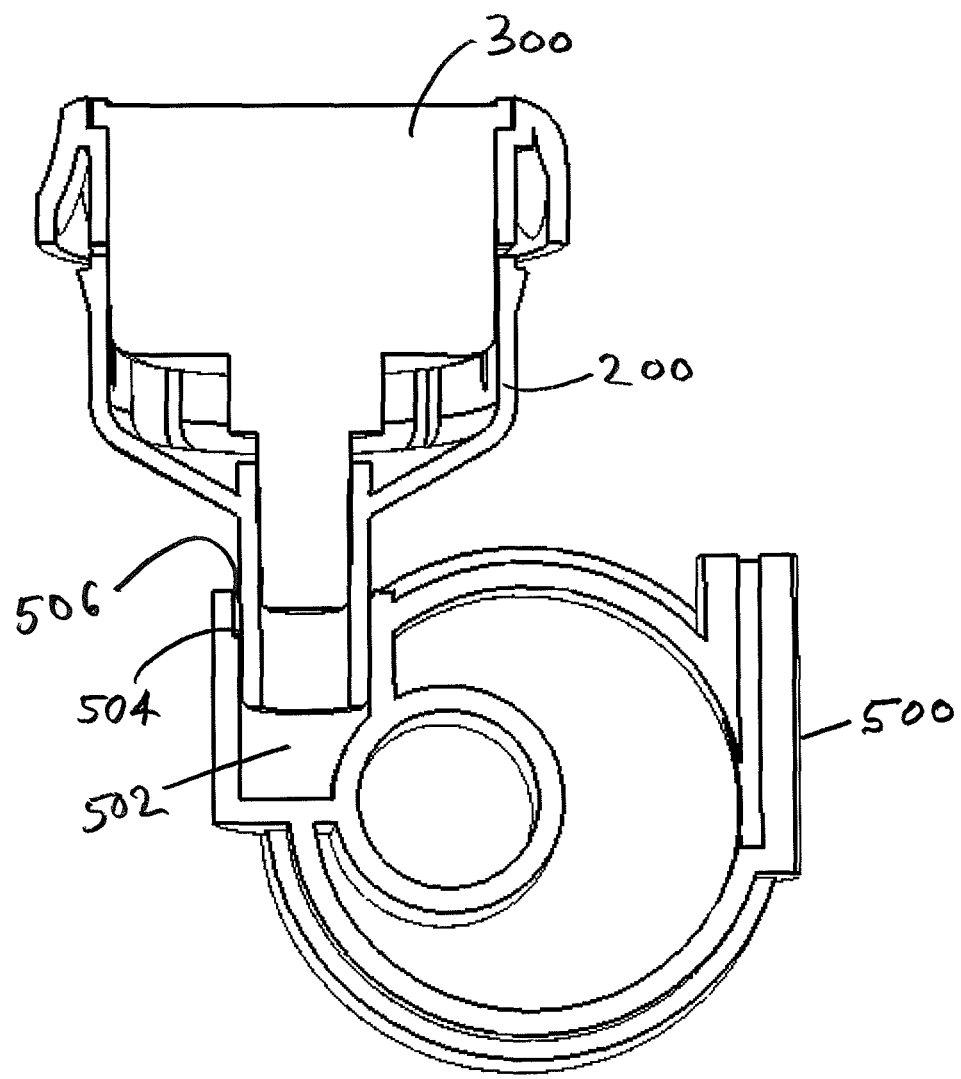
FIG. 6 shows a cross sectional view of the regulator/gauge assembly in place in the manifold of FIG. 5.

FIG. 6 shows manifold 500 with regulator/gauge assembly 100 inserted therein in cross section. It can be seen that shoulder 504 is shown on the left side of port 502. The portion of port 502 above shoulder 504 will have a diameter d2 while portion of port 502 below shoulder 504 will have a diameter d1. It should be noted that the shape and configuration of manifold 500 is not part of the invention as long as manifold 500 defines port 502 having sloped shoulder 504 in which boss 206 of regulator 200 is able to rotate. Port 502 need not even be defined in a manifold—it is within the scope of the invention that a customized pipe fitting may be utilized to hold regulator/gauge assembly 100.

In the preferred embodiment of the invention, sloped shoulder 504 varies linearly in height. However, it is possible that the height of the shoulder could vary around the inner-circumference of port 504. In other words, a portion of the helical shoulder 504 could have a first slope while a second portion of shoulder 504 could have a second slope, or shoulder 504 could be curved, thereby allowing the strength of the vacuum to vary at different rates as regulator/gauge assembly 100 is rotated within port 502. It is also possible that opening 208 defined in boss 206 of regulator 200 could have a shape which would define a different vacuum profile as the regulator 200 is rotated within port 502.

Figure 7:
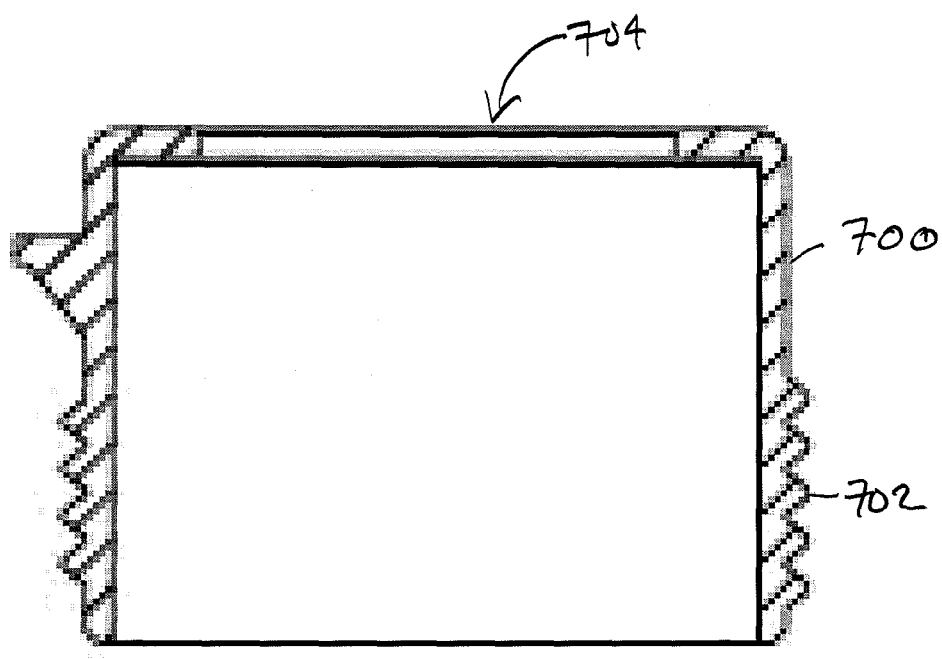
FIG. 7 shows one embodiment of a collar used to connect the regulator/gauge assembly to the housing of a device
Figure 8:
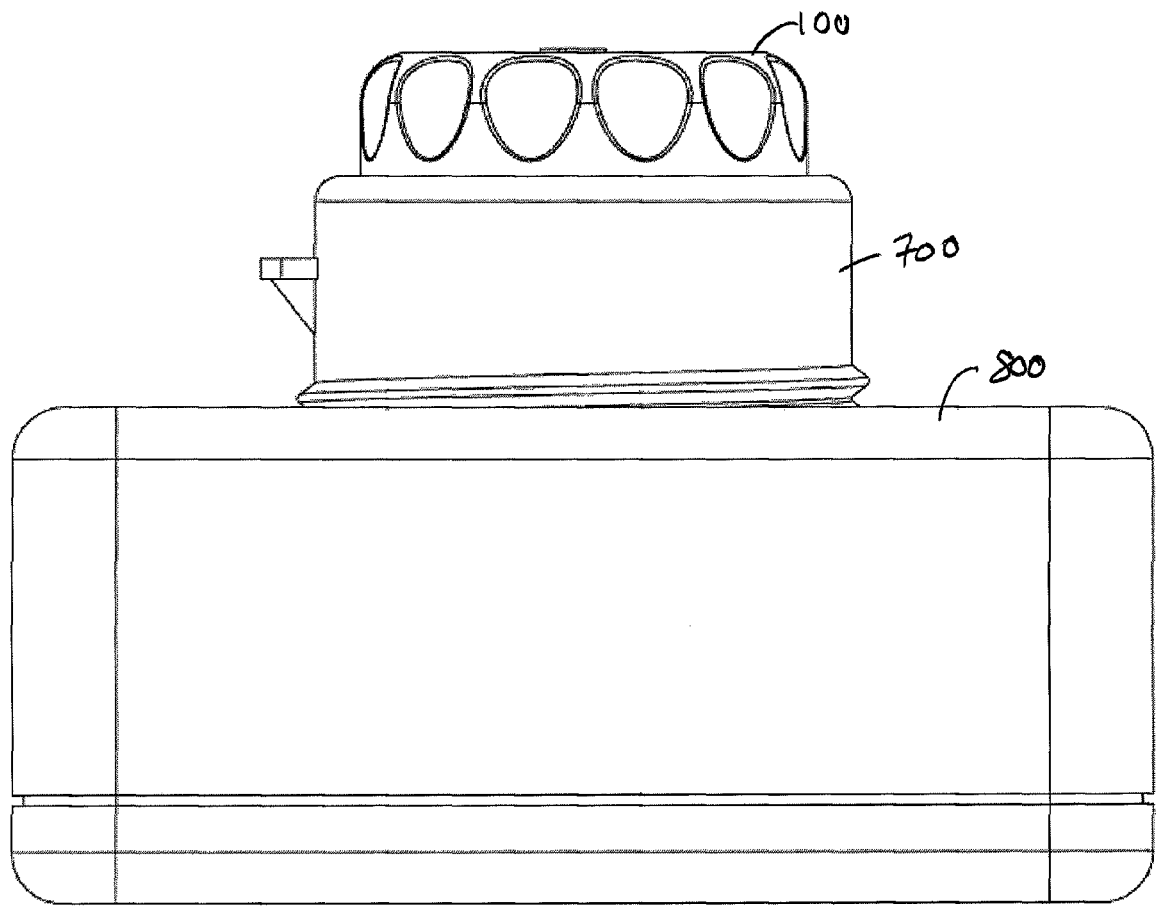
FIG. 8 shows the regulator/gauge assembly and the collar in place in a demonstration housing
Figure 9:
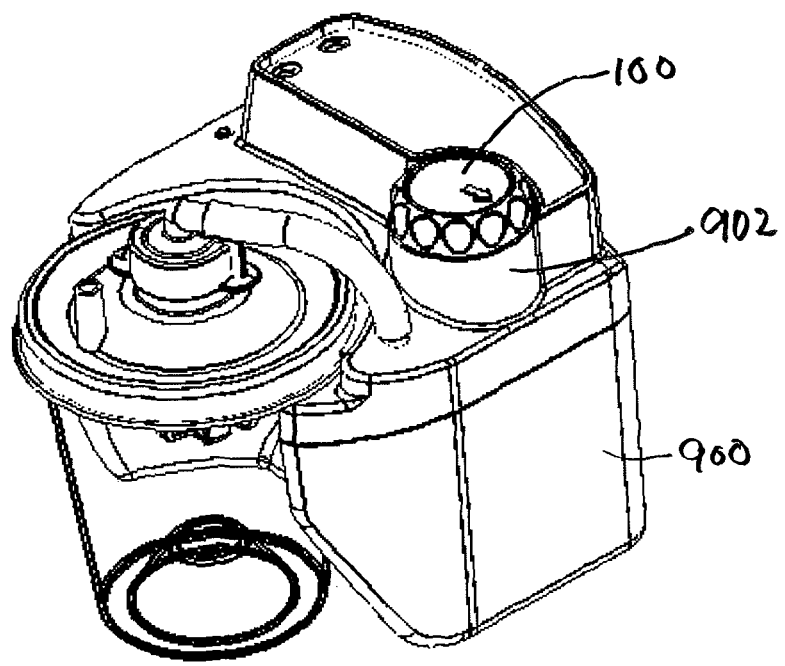
FIG. 9 shows the regulator/gauge assembly in place in an actual device.

Regulator/gauge assembly 100 will typically extend out of the housing of the device. A fitting for this purpose is shown FIG. 7, wherein regulator 200 would be inserted in opening 704 of fitting 700 and threaded area 702 of fitting 700 would contact the housing of the device in which the invention is installed. A demonstration of such a device is shown in FIG. 8, with 800 being the body of the device and 700 being the fitting just described and shown in FIG. 7. It can be seen that regulator gauge assembly is inserted therein and, secured axially by tabs 201, can be freely rotated within fitting 700. Fitting 700 may also be integral to the housing of the device FIG. 9 shows a more typical installation in which regulator/gauge assembly 100 is able to rotate within a portion 902 of the housing of the device especially designed for this purpose. The device shown I FIG. 9, by way of example, is an aspirator for aspirating the airway of a patient.

It should be noted that the fact that gauge 300 and regulator 200 rotate together in a concentric manner provides the effect of having the scale of gauge 300 move underneath needle 303 of gauge 300, which appears virtually stationary in the manner of a magnetic compass being rotated and having the directions move underneath the stationary needle. This makes the gauge easy to read from one position and also eliminates the need to have separate openings in the housing of device 900 for the gauge and the regulator.

In the preferred embodiment of the invention, regulator 200 is preferably composed of a polycarbonate material while the shoulder portion is preferable composed of a thermoplastic elastomer. However, it is possible to make the device of different materials including for example, metal.

In addition, it is not necessary that the shoulder be integral with the interior of the port 502 on manifold 500. It is possible instead that the shoulder could be provided by a separate bushing which is inserted into the port and is held stationary therein by an interference fit or some other type of fit with the interior surface of port 502.

It can be seen by one of skill in the art that some variations in this design are possible while still being within the spirit of the invention. For example, the shape of a regulator 200 maybe driven by the external shape of gauge 300 and by the space available within the device between the opening in the housing of the device for the regulator/gauge assembly 100 and the manifold 500. Additionally, it is not necessary that a manifold be present. The device may be attached directly to fittings, plumbing or piping in the vacuum system in much the same manner as a separate gauge and regulator might be utilized in such a system.

I claim:

1. A combination regulator and gauge for a vacuum device comprising:
   a. a vacuum gauge having a body portion and a stem portion;
   b. a regulator portion having a cylindrical body having a first portion of a first diameter tapering to a second portion of a second diameter, said vacuum gauge being disposed inside of and concentric with said regulator, said body portion of said gauge being inside said first portion of said regulator and said stem portion of said gauge being inside said second portion of said regulator;
   c. an opening, defined in said second portion of said regulator; and
   d. a sloped shoulder held adjacent said second portion of said regulator such that a rotation of said regulator will cause said shoulder to expose or cover varying portions of said opening.

2. The combination regulator and gauge of claim 1 wherein said opening is defined in a part of said second portion of said regulator which extends past the end of said stem portion of said gauge.

3. The combination regulator and gauge of claim 2 wherein said opening is a slot.

4. The combination regulator and gauge of claim 1 wherein said sloped shoulder is helical in shape.

5. The combination regulator and gauge of claim 1 wherein said sloped shoulder is defined on the inside surface of a cylindrical port into a vacuum chamber and further wherein said second portion of said regulator is disposed in said port and is able to rotate therein.

6. The combination regulator and gauge of claim 5 wherein said port defines a first inner diameter below said shoulder, said first inner diameter being the approximate diameter of the outer surface of said second body portion of said regulator; and further wherein said port defines a second inner diameter above said shoulder, said second inner diameter being larger than said first inner diameter.

7. The combination regulator and gauge of claim 6 wherein, as said regulator is rotated within said port, said sloped shoulder will cover or expose said opening, depending on the direction of rotation.

8. The combination regulator and gauge of claim 6 wherein the slope of said shoulder is non-linear.

9. The combination regulator and gauge of claim 6 further comprising a manifold and further wherein said cylindrical port is defined in the body of said manifold.

10. The combination regulator and gauge of claim 6 wherein part of said first portion of said regulator extends through an opening in a housing of said vacuum device.

11. The combination regulator and gauge of claim 10 further comprising a beveled portion defined on the part of said first portion of said regulator which extends through the opening in the housing of said vacuum device.

12. The combination regulator and gauge of claim 11 wherein rotating said beveled portion causes said regulator to rotate within said port.

13. The combination regulator and gauge of claim 6 wherein said opening is shaped to provide a specific vacuum profile as said regulator is rotated.

14. The combination regulator and gauge of claim 6 wherein said shoulder is shaped to provide a specific vacuum profile as said regulator is rotated.

15. The combination regulator and gauge of claim 6 wherein said opening and said shoulder are shaped to provide a specific vacuum profile as said regulator is rotated.

16. A vacuum device comprising:
 a. a housing, defining an opening therein;
 b. a manifold, located within said housing, said manifold defining a circular port therein;
 c. a vacuum source, connected to said manifold.
 d. a combination regulator and gauge, said gauge being concentrically mounted within said regulator, said regulator defining a portion adapted to engage said port and rotate therein, said combination regulator and gauge extending through said opening defined in said housing;
 e. a sloped shoulder, defined on the inner surface of said port, said port defining a first inner diameter below said shoulder, said first inner diameter being the approximate diameter of the outer surface of the portion of said regulator adapted to engage said port, said port defining a second inner diameter above said shoulder, said second inner diameter being larger than said first inner diameter; and
 f. an opening, defined in said portion of said regulator adapted to engage said port, said opening being exposed or covered by said inner surface of said port having said first diameter as said sloped shoulder moves over said opening when said regulator is rotated with said port.

17. The vacuum device of claim 16 wherein the strongest vacuum is delivered when said opening is completely covered by said portion of said port defining said first inner diameter.

18. The vacuum device of claim 16 wherein the weakest vacuum is delivered when said opening is completely uncovered and air is allowed to enter said opening through said portion of said port defining said second inner diameter.

19. The vacuum device of claim 16 wherein said regulator and said gauge are rotated together.

20. The vacuum device of claim 16 further defining a beveled portion, located on the portion of said regulator extending through said opening defined in said housing.

* * * * *

UNITED STATES PATENT AND TRADEMARK OFFICE
CERTIFICATE OF CORRECTION

PATENT NO. : 8,555,727 B2  
APPLICATION NO. : 13/158680  
DATED : October 15, 2013  
INVENTOR(S) : Joel David Neatrour Page 1 of 1

It is certified that error appears in the above-identified patent and that said Letters Patent is hereby corrected as shown below:

In the Claims

In Claim 16, paragraph (f)

In Column 6, Line 20:
Please delete
"opening when said regulator is rotated with said port."
and replace with
--opening when said regulator is rotated with respect to said port.--

Signed and Sealed this
Tenth Day of February, 2015

Michelle K. Lee
*Deputy Director of the United States Patent and Trademark Office*